(12) United States Patent
Groninger et al.

(10) Patent No.: US 9,881,510 B2
(45) Date of Patent: Jan. 30, 2018

(54) TESTING SYSTEM AND METHOD

(71) Applicant: General Electric Company, Schenectady, NY (US)

(72) Inventors: Daniel Scott Groninger, Port Royal, PA (US); Robert Carroll Ward, State College, OH (US); Francois Xavier de Fromont, State College, PA (US); Chad Martin Shaffer, State College, PA (US)

(73) Assignee: General Electric Company, Schenectady, NY (US)

( * ) Notice: Subject to any disclaimer, the term of this patent is extended or adjusted under 35 U.S.C. 154(b) by 1095 days.

(21) Appl. No.: 13/725,091

(22) Filed: Dec. 21, 2012

(65) Prior Publication Data

US 2014/0178853 A1 Jun. 26, 2014

(51) Int. Cl.
G01N 29/04 (2006.01)
G09B 5/00 (2006.01)
G01N 29/22 (2006.01)
G09B 19/24 (2006.01)

(52) U.S. Cl.
CPC ............ G09B 5/00 (2013.01); G01N 29/04 (2013.01); G01N 29/22 (2013.01); G09B 19/24 (2013.01)

(58) Field of Classification Search
CPC ...... G01M 5/005; G01M 5/00; G01M 5/0041; G01M 5/0075; G01M 5/0083; G01M 5/0091; G01M 5/0033; G09B 25/00; G09B 25/02; G01N 29/04
See application file for complete search history.

(56) References Cited

U.S. PATENT DOCUMENTS

| | | | |
|---|---|---|---|
| 4,093,382 A | 6/1978 | Kurtz | |
| 4,476,434 A | 10/1984 | Collins et al. | |
| 6,285,447 B1 | 9/2001 | Parker et al. | |
| 7,436,504 B2 | 10/2008 | Shaw et al. | |
| 8,310,533 B2 | 11/2012 | Morse et al. | |
| 2002/0038163 A1* | 3/2002 | Hazama | G05B 19/4097 700/165 |
| 2003/0163219 A1 | 8/2003 | Flesher | |
| 2005/0035752 A1 | 2/2005 | Bertness et al. | |
| 2007/0225931 A1 | 9/2007 | Morse et al. | |
| 2008/0147347 A1 | 6/2008 | Shaw et al. | |
| 2009/0149972 A1* | 6/2009 | Nasle | G05B 17/02 700/80 |
| 2009/0307628 A1* | 12/2009 | Metala | G06T 7/0006 715/782 |

(Continued)

OTHER PUBLICATIONS

Search report from PCT/US2013/072631 dated Apr. 11, 2014.

*Primary Examiner* — Bruk Gebremichael
(74) *Attorney, Agent, or Firm* — Fletcher Yoder, P.C.

(57) ABSTRACT

A testing system for use in conducting testing of a structure, and a method for configuring a testing system are provided. The testing system includes a testing device that includes a presentation interface, a user input interface, a memory device and a processor coupled in communication with the presentation interface, the user input interface, and the memory device. The processor causes the testing device to present to a user, prior to a test session, at least one demonstrative instruction for conducting a test session using the testing device, and at least one test instruction for use while the user is conducting a test session using the device.

11 Claims, 5 Drawing Sheets

(56) References Cited

U.S. PATENT DOCUMENTS

| | | |
|---|---|---|
| 2010/0100344 A1 | 4/2010 | Patel et al. |
| 2011/0183304 A1* | 7/2011 | Wallace .................. G09B 19/24 |
| | | 434/234 |
| 2011/0238336 A1* | 9/2011 | Di Scalea ............ G01N 29/043 |
| | | 702/56 |
| 2011/0252888 A1* | 10/2011 | Goodman ........... G01M 13/028 |
| | | 73/593 |
| 2011/0270525 A1 | 11/2011 | Hunter |
| 2012/0041697 A1 | 2/2012 | Stukenberg |
| 2012/0265491 A1 | 10/2012 | Drummy |

\* cited by examiner

TESTING SYSTEM AND METHOD

BACKGROUND OF THE INVENTION

The present disclosure relates generally to testing systems for use in testing physical characteristics of structures, and, more particularly, to methods for configuring and using testing systems.

Frequently, testing devices, for use in non-destructive testing ("NDT") of structures, for example, are configured to perform a variety of testing functions, or are configured to be used in a plurality of different operating modes. Selection and implementation of testing functions or operating modes by a user (or "test operator") is often dependent upon testing conditions, such as the type or configuration of the structure being tested, and the characteristics or phenomena to be detected during the test. However, while such testing devices may be capable of performing a wide variety of functions, such testing devices are typically passive in nature, in that proper operation of the testing devices and/or proper procedure for conducting specific tests with the testing devices may not be readily discernible from the testing devices. Such testing devices rely upon a relatively high degree of expertise on the part of a test operator. Without prior experience in operating such testing devices, a test operator may be required to refer to separately maintained guides and instruction manuals, records of historical testing data, and/or advisory input from other, experienced test operators in order to perform a test adequately and achieve desired results.

Accordingly, it would be desirable to provide testing devices that are configured to enable an inexperienced test operator to perform tests with the testing devices, without the need to rely upon resources external to the testing devices.

BRIEF DESCRIPTION OF THE INVENTION

In one embodiment, a testing system for use in conducting testing of a structure is provided. The testing system includes a testing device that includes a presentation interface, a user input interface, a memory device, and a processor coupled in communication with the presentation interface, the user input interface, and the memory device. The processor is programmed to cause the testing device to present to a user, prior to a test session, at least one demonstrative instruction for conducting a test session using the testing device. The processor is also programmed to cause the testing device to present to the user during a test session, at least one test instruction for use of the testing device.

In another embodiment, a method for configuring a testing device is provided. The testing device includes a memory device. The method includes storing, in the memory device, data representing at least one demonstrative instruction for conducting a test session using the testing device, for presentation to a user prior to a test session. The method also includes storing, in the memory device, data representing at least one test instruction, for presentation to a user during a test session.

In yet another embodiment, a testing device for conducting testing of a structure is provided. The testing device includes a sensor, a presentation interface, a user input interface, a memory device, and a processor coupled in communication with the sensor, the presentation interface, the user input interface, and the memory device. The processor is programmed to cause the testing device to present to a user, prior to a test session, at least one demonstrative instruction for conducting a test session using the testing device. The processor is also programmed to cause the testing device to present to the user during a test session at least one test instruction for use of the testing device.

DETAILED DESCRIPTION OF THE INVENTION

Although specific features of various embodiments of the invention may be shown in some drawings and not in others, this is for convenience only. In accordance with the principles of the invention, any feature of a drawing may be referenced and/or claimed in combination with any feature of any other drawing.

The methods and systems described herein are useful for configuring a testing device for providing guidance to a user prior to, and during testing procedures. The methods and systems described herein may be implemented using computer programming or engineering techniques including computer software, firmware, hardware or any combination or subset thereof, wherein the technical effects may be achieved by performing at least one of the following steps: a) storing, in a memory device, data representing at least one demonstrative instruction for conducting a test session using the testing device, for presentation to a user prior to a test session; b) storing, in the memory device, data representing at least one test instruction to a user during a test session; c) coupling a base computing device to the testing device; d) transferring from the base computing device to the testing device at least one data file containing data representing at least one of the at least one demonstrative instruction and the at least one test instruction; e) storing, in the memory device, data representing at least one calibration instruction for use in calibrating said testing device; f) storing, in the memory device, data representing at least one report preparation instruction for use in preparing a report of results obtained during a test session; g) coupling a sensor in communication with a processor associated with the testing device; and h) coupling the presentation interface and the user input interface together as a touchscreen.

Figure 1:
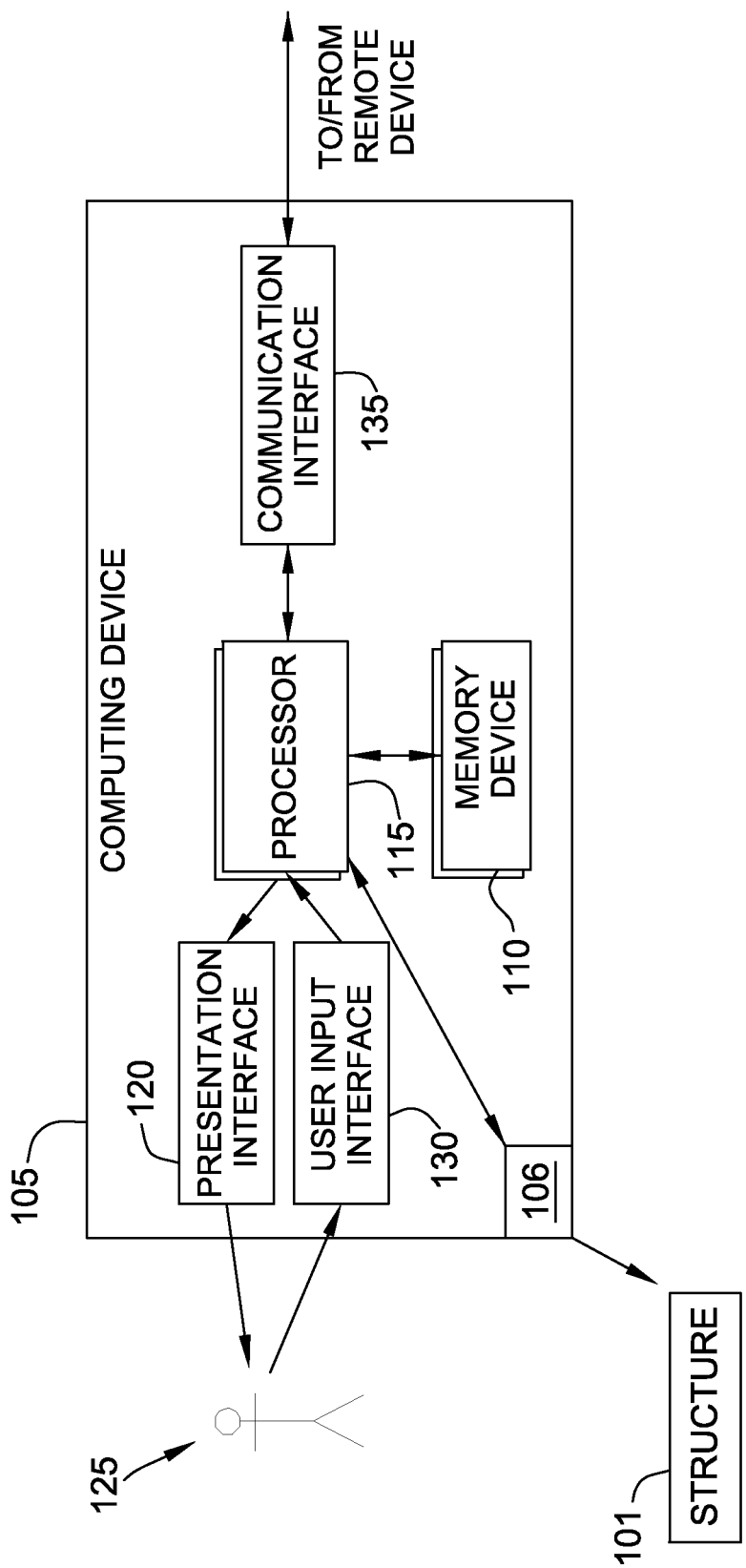
FIG. 1 is a block diagram of a known computing device for use in operating testing instruments.

FIG. 1 is a schematic block diagram of a known computing device 105 that may be used to conduct testing, such as non-destructive testing of a structure 101. In some known examples, computing device 105 is a data collection device. Computing device 105 includes one or more sensors 106, a memory device 110 and a processor 115 operatively coupled to memory device 110 for executing instructions. In some embodiments, executable instructions are stored in memory device 110. Computing device 105 is configurable to perform one or more operations described herein by programming processor 115. In some known examples, processor 115 is programmed by encoding an operation as one or more executable instructions and providing the executable instructions in memory device 110. In some known examples, processor 115 includes one or more processing units (e.g., in a multi-core configuration).

In some known computing devices 105, memory device 110 is configured to store operational measurements including, without limitation, vibration readings, field voltage and current readings, field reference set points, stator voltage and current readings, rotor speed readings, maintenance tasks, and/or any other type of data. In some known computing devices 105, processor 115 removes or "purges" data from memory device 110 based on the age of the data. For example, processor 115 may overwrite previously recorded and stored data associated with a subsequent time and/or event. In addition, or alternatively, processor 115 may remove data that exceeds a predetermined time interval.

Some known computing devices 105 include a presentation interface 120 communicatively coupled to processor 115. Presentation interface 120 presents information, such as a user interface and/or an alarm, to a user 125. For example, presentation interface 120 may include a display adapter (not shown) that may be coupled to a display device (not shown), such as a cathode ray tube (CRT), a liquid crystal display (LCD), an organic LED (OLED) display, and/or an "electronic ink" display. Presentation interface 120 includes one or more display devices. In addition, or alternatively, presentation interface 120 may include an audio output device (not shown) (e.g., an audio adapter and/or a speaker) and/or a printer (not shown).

Some known computing devices 105 include a user input interface 130, which is communicatively coupled to processor 115 and receives input from user 125. User input interface 130 includes, for example, a keyboard, a pointing device, a mouse, a stylus, a touch sensitive panel (e.g., a touch pad or a touch screen), a gyroscope, an accelerometer, a position detector, and/or an audio input interface (e.g., including a microphone). A single component, such as a touch screen, may function as both a display device of presentation interface 120 and user input interface 130.

In some known computing devices 105, a communication interface 135 is coupled to processor 115 and is configured to be coupled in communication with one or more other devices, such as a sensor or another computing device 105, and to perform input and output operations with respect to such devices. For example, communication interface 135 may include, without limitation, a wired network adapter, a wireless network adapter, a mobile telecommunications adapter, a serial communication adapter, and/or a parallel communication adapter. Communication interface 135 may receive data from and/or transmit data to one or more remote devices. For example, a communication interface 135 of one computing device 105 may transmit an alarm to the communication interface 135 of another computing device 105.

Figure 2:
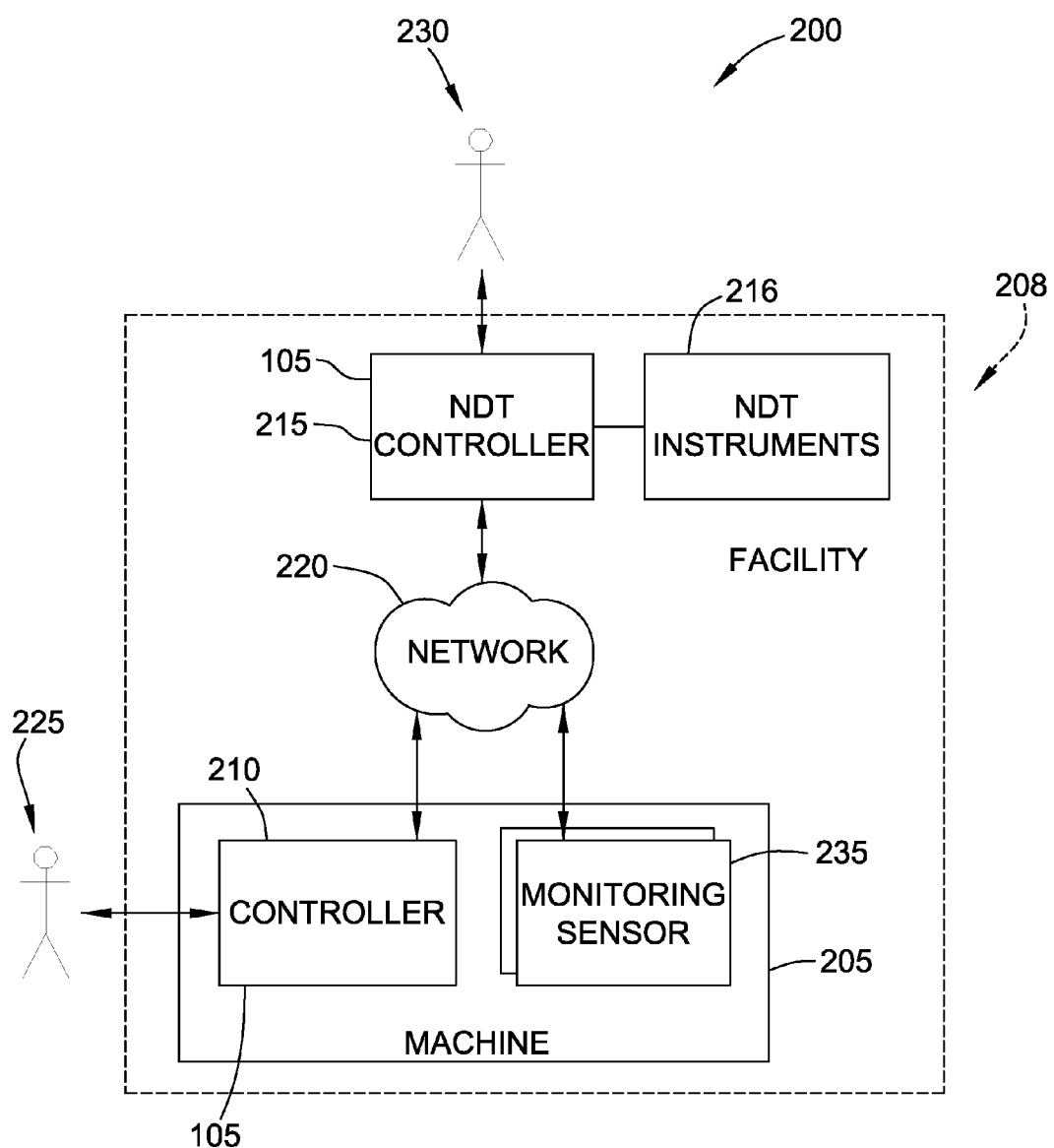
FIG. 2 is a block diagram of a known monitoring system that may be used with computing device shown in FIG. 1.

FIG. 2 is a block diagram of a known system 200 that may be used to monitor and/or operate a machine 205. System 200 may be a data acquisition system (DAS) and/or a supervisory control and data acquisition system (SCADA). Machine 205 may be any industrial equipment for use with any industrial process, including, without limitation, a chemical process reactor, a heat recovery steam generator, a steam turbine, a gas turbine, a switchyard circuit breaker, and a switchyard transformer. In some known examples, machine 205 is a component of a larger, integrated industrial facility 208. Facility 208 may include, without limitation, multiple machines 205. Also, in some known examples, system 200 includes a machine controller 210 and a nondestructive testing (NDT) instrument controller 215 coupled together in communication via a network 220.

Machine controller 210 and/or NDT controller 215 may be computing devices 105. In addition, each computing device 105 may be coupled to network 220 via communication interface 135. Alternatively, in some known examples, controller 210 is integrated with controller 215.

Controller 210 is configured to interact with a first operator 225 (e.g., via user input interface 130 and/or via presentation interface 120). For example, controller 210 may present information about machine 205, such as alarms, to operator 225. NDT controller 215 also interacts with a second operator 230 (e.g., via user input interface 130 and/or presentation interface 120) through network 220. For example, NDT controller 215 may present alarms and/or maintenance tasks to second operator 230. As used herein, the term "operator" includes any person in any capacity associated with operating and maintaining facility 208, including, without limitation, shift operations personnel, maintenance technicians, and facility supervisors.

In some known examples, machine 205 includes one or more monitoring sensors 235 and NDT instruments 216 in communication directly or indirectly with network 220. Monitoring sensors 235 or NDT instruments 216 collect operational measurements such as, without limitation, vibration readings, field voltage and current readings, field reference set points, stator voltage and current readings, rotor speed readings, maintenance tasks, and/or any other type of data. Monitoring sensors 235 repeatedly (e.g., periodically, continuously, and/or upon request) transmit operational measurement readings in real-time or near real-time. As used herein, real-time refers to outcomes occurring at a substantially short period after a change in the inputs affecting the outcome, for example, receiving operational measurement data, receiving NDT measurement data, transmitting processed data or further processing. The period is the amount of time elapsed between successive iterations of a regularly repeated task or between one task and another. The time period is a result of design parameters of the real-time system that may be selected based on the importance of the outcome and/or the capability of the system implementing processing of the inputs to generate the outcome. Additionally, events occurring in real-time occur without substantial intentional delay, although circuit latencies or transmission delays may introduce unwanted delay. Such data is transmitted across network 220 and may be accessed by any device capable of accessing network 220 including, without limitation, desktop computers, laptop computers, and personal digital assistants (PDAs) (none shown). Transmissions may be selectively directed to any computing device 105 in communication with network 220, e.g., NDT controller 215 or controller 210.

Facility 208 may include additional monitoring sensors (not shown) that are similar to monitoring sensors 235 that collect operational data measurements associated with the remainder of facility 208. Such additional sensors may measure data from redundant machines 205 and/or facility environmental data, including, without limitation, local wind speed, local wind velocity, and ambient temperatures.

As described herein, users (also known as "test operators") that conduct tests, and in particular, nondestructive testing, "in the field" may be inexperienced with testing procedures generally, or may be unfamiliar with a specific computing device 105 and the test(s) for which the specific computing device 105 is used. Users operating computing device(s) 105 often are required to consult separate instruction manuals and/or guidance from other, more experienced users, in order to obtain desired test results. Furthermore, the presence of the more experienced user, accompanying the inexperienced user in the field, has the additional effect of increasing manpower requirements for testing procedures. Accordingly, it would be desirable to provide a computing device, specifically, a field testing device that facilitates operation by inexperienced users, without requiring reference to external resources, such as instruction or operation manuals, or consultation with users having prior or greater experience with the field testing device.

Figure 3:
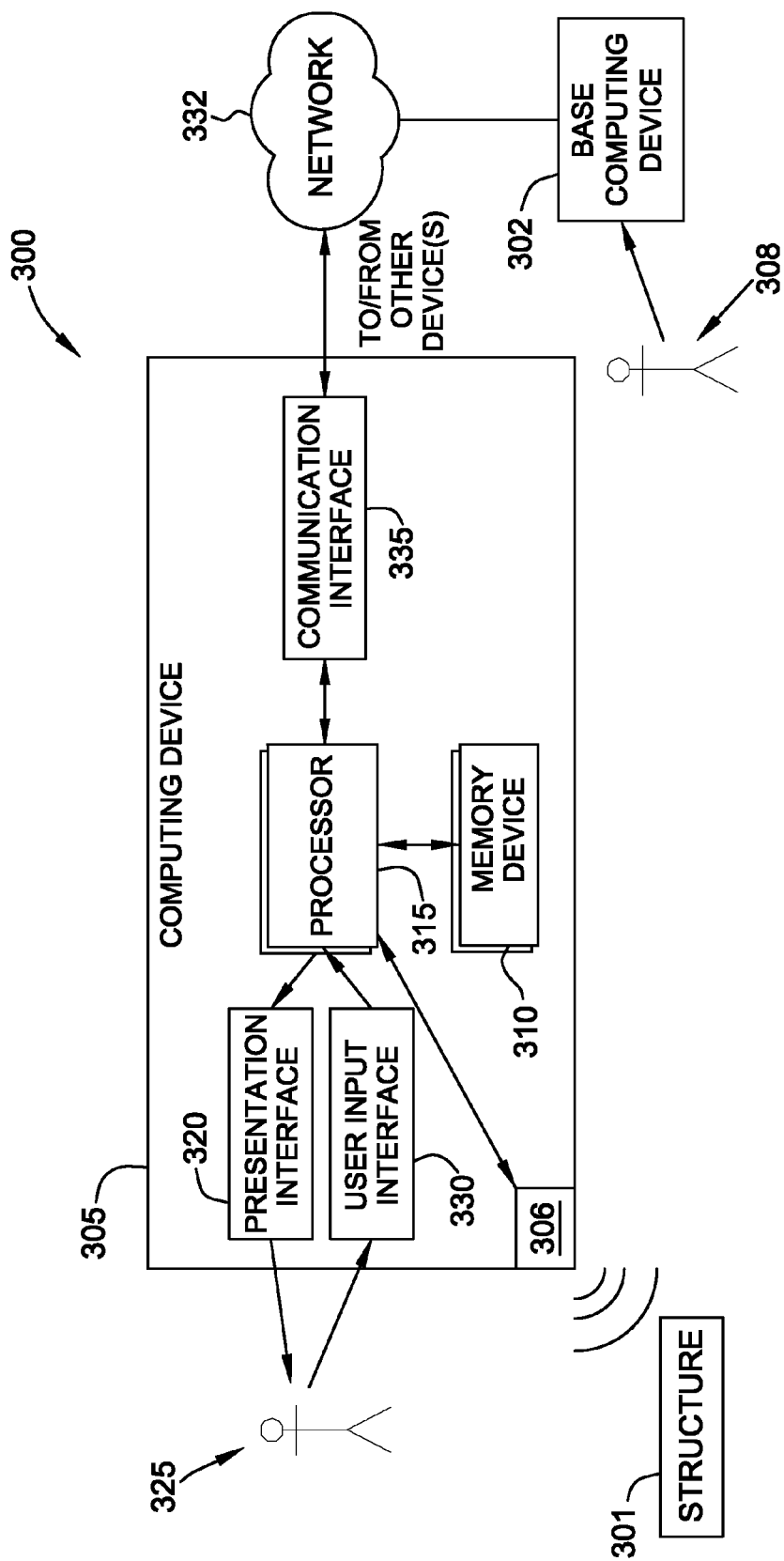
FIG. 3 is a block diagram of an exemplary computing device for use in conducting testing procedures.

FIG. 3 is a schematic block diagram of an exemplary testing system 300 that includes field testing device 305 that may be used to perform tests on a structure 301. In the exemplary embodiment, field testing device 305 is a data collection device and includes at least one sensor 306, a memory device 310 and a processor 315 operatively coupled to memory device 310 for executing instructions. In some embodiments, executable instructions are stored in memory device 310. Field testing device 305 is configurable to perform one or more operations described herein by programming processor 315. For example, processor 315 may be programmed by encoding an operation as one or more executable instructions and providing the executable instructions in memory device 310. Processor 315 may include one or more processing units (e.g., in a multi-core configuration).

In the exemplary embodiment, sensor 306 is a sensory transducer, such as an electromagnetic sensor or an ultrasonic transceiver, which is configured to emit sensory emanations and receive emanations that are affected by structure 301 being sensed. In other embodiments, sensor 306 may be a visible light imaging device (such as a still image camera, video camera or borescope), an infrared imaging device (such as a still image camera or video camera), an X-ray imaging apparatus (configured to generate and emit and/or receive X-rays), or other imaging or sensory device. Comparison and analysis of emitted and received sensory emanations provides information regarding a characteristic of structure 301.

As used herein, the term "processor" is not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include a scanner. Furthermore, in the exemplary embodiment, additional output channels may include, but not be limited to, an operator interface monitor.

In the exemplary embodiment, field testing device 305 is configured as an integral unit. In other embodiments, one or more components of field testing device 305 may be substantially separate, or separable from, other components of field testing device 305. For example, sensor 306 may be configured as one or more components separate from the remaining components of field testing device 305, but functionally connected thereto, for example by a hardwired connection, or by a wireless connection, such as a Wi-Fi or Bluetooth®-type connection. Sensor 306 may be any type of sensory apparatus, such as, but not limited to, electromagnetic, optical, and/or acoustic transducers, that permits field testing device 305 to function as described herein. In addition, while exemplary embodiments described herein may describe field testing device 305 as being a portable, hand-held device, the present disclosure is not limited to portable devices. Non-portable, or even fixed testing devices configured to enable the systems and methods to function as described herein, may be used.

Memory device 310 may be configured to store data acquired through use of field testing device 305, without limitation, acoustic field readings, magnetic field readings, vibration readings, field voltage and current readings, field reference set points, stator voltage and current readings, rotor speed readings, maintenance tasks, and/or any other type of data. In some embodiments, processor 315 removes or "purges" data from memory device 310 based on the age of the data. For example, processor 315 may overwrite previously recorded and stored data associated with a subsequent time and/or event. In addition, or alternatively, processor 315 may remove data that exceeds a predetermined time interval.

In various embodiments, field testing device 305 includes a presentation interface 320 communicatively coupled to processor 315. Presentation interface 320 presents information, such as a user interface and/or an alarm, to a user 325. For example, presentation interface 320 may include a display adapter (not shown) that may be coupled to a display device (not shown), such as a cathode ray tube (CRT), a liquid crystal display (LCD), an organic LED (OLED) display, and/or an "electronic ink" display. In some embodiments, presentation interface 320 includes one or more display devices. In addition, or alternatively, presentation interface 320 may include an audio output device (not shown) (e.g., an audio adapter and/or a speaker) and/or a printer (not shown). In some embodiments, field testing device 305 includes a user input interface 330. In the exemplary embodiment, user input interface 330 is communicatively coupled to processor 315 and receives input from user 325. User input interface 330 may include, for example, a keyboard, a pointing device, a mouse, a stylus, a touch sensitive panel (e.g., a touch pad or a touch screen), a gyroscope, an accelerometer, a position detector, and/or an audio input interface (e.g., including a microphone). A single component, such as a touch screen, may function as both a display device of presentation interface 320 and user input interface 330. In an exemplary embodiment, particularly in an embodiment in which field testing device 305 is configured as a portable or hand-held device, presentation interface 320 and user input interface 330 are combined such as in a combined touch screen and visual display device 350 (illustrated in FIGS. 4A and 4B), that is configured for full touch screen capabilities, such as the ability to respond to gestures (for example, sliding fingertip and thumb together on a screen surface to "shrink" an image displayed thereon). In addition, in the exemplary embodiment, the test application enables user 325 to use touch screen 350 to enter and record notes as well as test data, stored in memory device 310. This eliminates the need for separate notebooks or other recording materials.

A communication interface 335 is coupled to processor 315 and is configured to be coupled in communication with one or more other devices, such as a sensor or another field testing device 305, and to perform input and output operations with respect to such devices. For example, communication interface 335 may include, without limitation, a wired network adapter, a wireless network adapter, a mobile telecommunications adapter, a serial communication adapter, and/or a parallel communication adapter. Communication interface 335 may receive data from and/or transmit data to one or more remote devices. For example, a communication interface 335 of one field testing device 305 may transmit test data to the communication interface 335 of another field testing device 305. In the exemplary embodiment, communication interface 335 enables field testing device 305 to connect to a network 332, to in turn connect to other devices, such as a base computing device 302. In alternative embodiments, communication interface 335 enables field testing device 305 to connect directly to other devices, such as a base computing device 302. In the exemplary embodiment, field testing device 305 is configured to present to user 325 both static and motion video images, using configuration and data files that have been preloaded into field testing device 305 from base computing device 302, or downloaded at a later time, for example over network 332.

Presentation interface 320 and/or communication interface 335 are both capable of providing information suitable for use with the methods described herein (e.g., to user 325 or another device). Accordingly, presentation interface 320 and communication interface 335 may be referred to as output devices. Similarly, user input interface 330 and communication interface 335 are capable of receiving information suitable for use with the methods described herein and may be referred to as input devices.

As previously described, in some circumstances, user 325 may not have prior experience using field testing device 305 to perform a particular type of test. Accordingly, in an exemplary embodiment, field testing device 305 is provided with a configurable user interface for providing an instructional environment to a user 325, both prior to and, in some embodiments, during a testing procedure. In the exemplary embodiment, field testing device 305 is provided with one or more applications, at least one of which is a test application. For example, field testing device 305 may be configured to perform electromagnetic testing (for example, eddy current weld testing). In the exemplary embodiment, the test applications that field testing device 305 implements include a series of images, which may be static images or "slides", or video clips, that are analogous to the slides or other images in a PowerPoint®-type presentation. In some embodiments, some images may be instructional, with text, drawings, pictures or even video to guide user 325 in connecting field testing device 305, locating an area to test on structure 301 (for example, identifying where on an aircraft to check a rivet line, or how to find a particular weld on a pipeline). Other screens may include user-operable controls or data views. Some images may combine both instructional materials and user-operable controls, for example, illustrating an image of an exemplary simulated data view, with an actual live data view displayed side-by-side with the exemplary simulated data view for comparison. In exemplary embodiments, the test applications include setup parameter values for field testing device 305, as well as instructional material for user 325, and controls that enable user 325 to select values for setup parameters. In alternative embodiments, after an application is downloaded into field testing device 305, the application causes field testing device 305 to apply one or more predefined setup parameters without further interaction required from user 325.

Figure 4A:
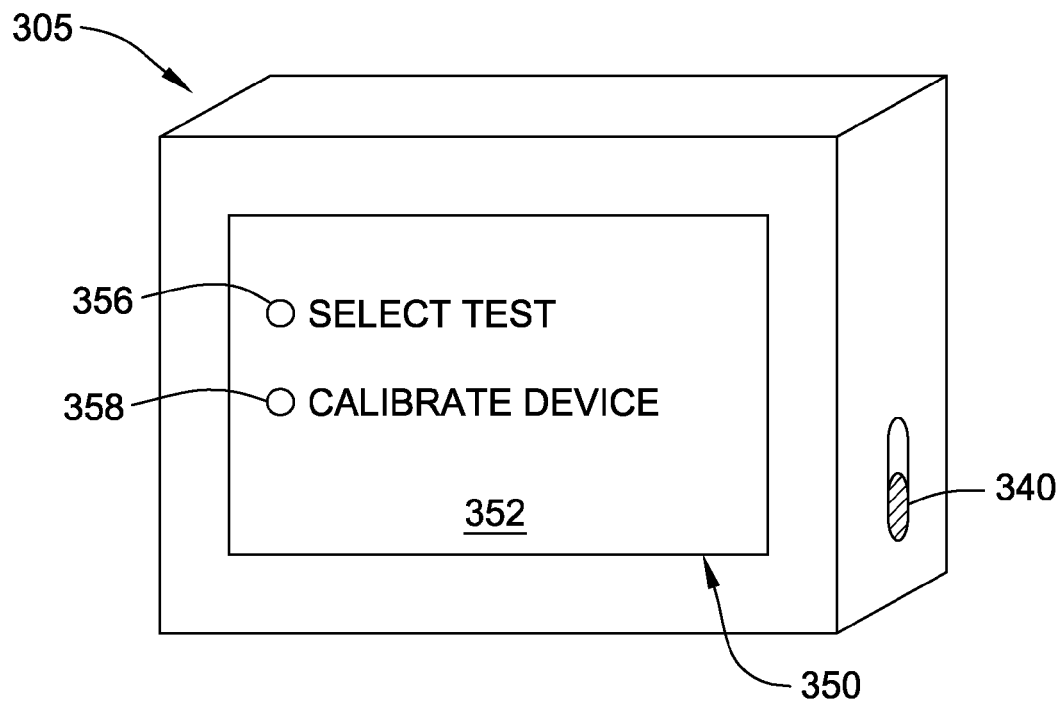
FIG. 4A is a front view of an exemplary computing device showing a representative display image.
Figure 4B:
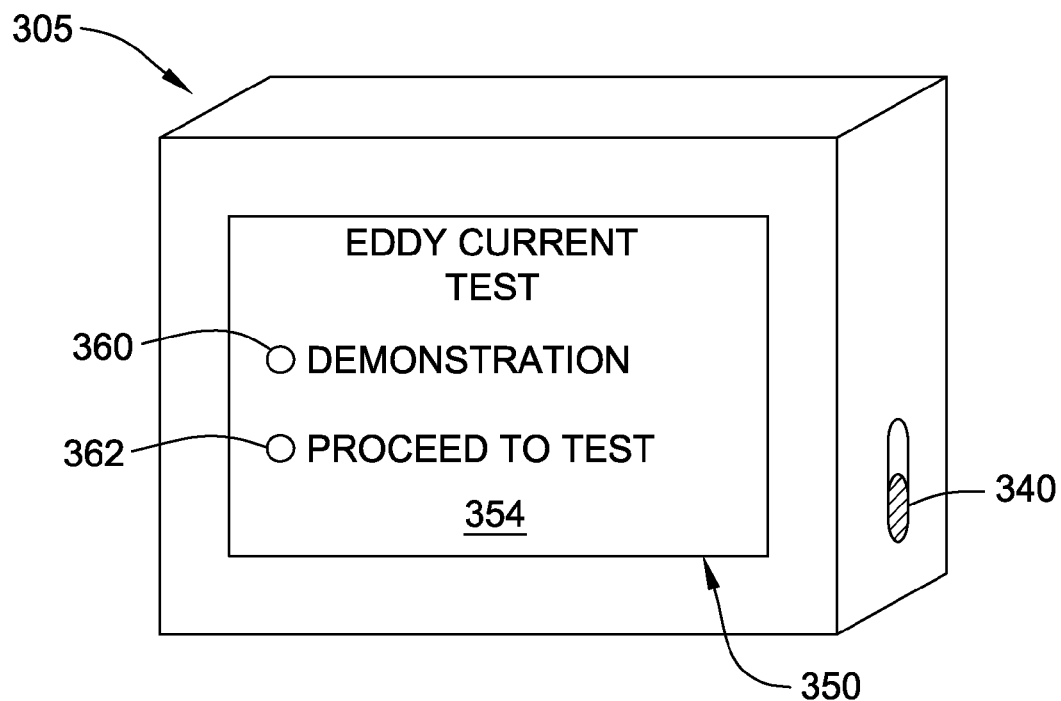
FIG. 4B is another front view of the exemplary computing device shown in FIG. 4A, showing another representative display image.

FIG. 4A is a perspective view of field testing device 305, showing a representative display image 352, presented on full-functionality touch screen 350. FIG. 4B is another perspective view of field testing device 305, illustrating another representative display image 354, presented on touch screen 350. Field testing device 305 includes, in an exemplary embodiment, a physical ON/OFF switch 340, which may be of any suitable configuration that enables field testing device 305 to function as described herein. In an exemplary embodiment, after user 325 turns on field testing device 305 and opens the test application, the test application causes field testing device 305 to display on touch screen 350 an opening screen that prompts user 325 to select (e.g., by touching a "button" displayed on touch screen 350) among a plurality of actions, for example, to select 356 a test to perform, or to calibrate 358 field testing device 305 (both shown in FIG. 4A). In the exemplary embodiment, if, for example, "SELECT TEST" 356 is selected, the test application then causes field testing device 305 to display subsequent display image 354 (shown in FIG. 4A) prompting user 325 to select among another plurality of actions, for example, to select DEMONSTRATION 360 (selection of which causes field testing device 305 to present to user 325 an instructional session including demonstrative instructions directed to the selected test), or to proceed 362 directly to the test procedure.

In the exemplary embodiment, if user 325 selects "DEMONSTRATION" 360, the test application causes field testing device 305 to display an image or series of images illustrating predefined steps for conducting the selected test. The image or series of images may be slides or a moving video image, and may be accompanied by text captioning and/or audio commentary. The series of images may address such aspects of operation of field testing device 305 as calibration of field testing device 305, gaining access to a location on structure 301 to be tested, performing treatment of a surface on structure 301, proper placement or manipulation of field testing device 305 before or during a testing procedure, and any required post-testing procedures, such as report or data preparation and transmission. In the exemplary embodiment, upon conclusion of the instructional session, the test application causes field testing device 305 to shift into an actual test mode of operation, enabling user 325 to proceed with an actual test procedure. Upon completion of the actual test procedure, the test application may cause field testing device 305 to present further display images with further courses of action, such as, but not limited to, uploading data to another device or to network 220 (shown in FIG. 2), preparing a report, or performing maintenance or shutdown procedures on field testing device 305. In the exemplary embodiment, the test application causes field testing device 305 to present user 325 with a series of choices at various stages of operation. In alternative embodiments, the test application is configured to present a series of images and corresponding actions in a fixed order, such as an instructional stage, a calibration stage, an actual test stage, and a reporting stage. The foregoing are merely examples of instructional and/or test operations features included in the test application, and the disclosure is not limited thereby.

Figure 5:
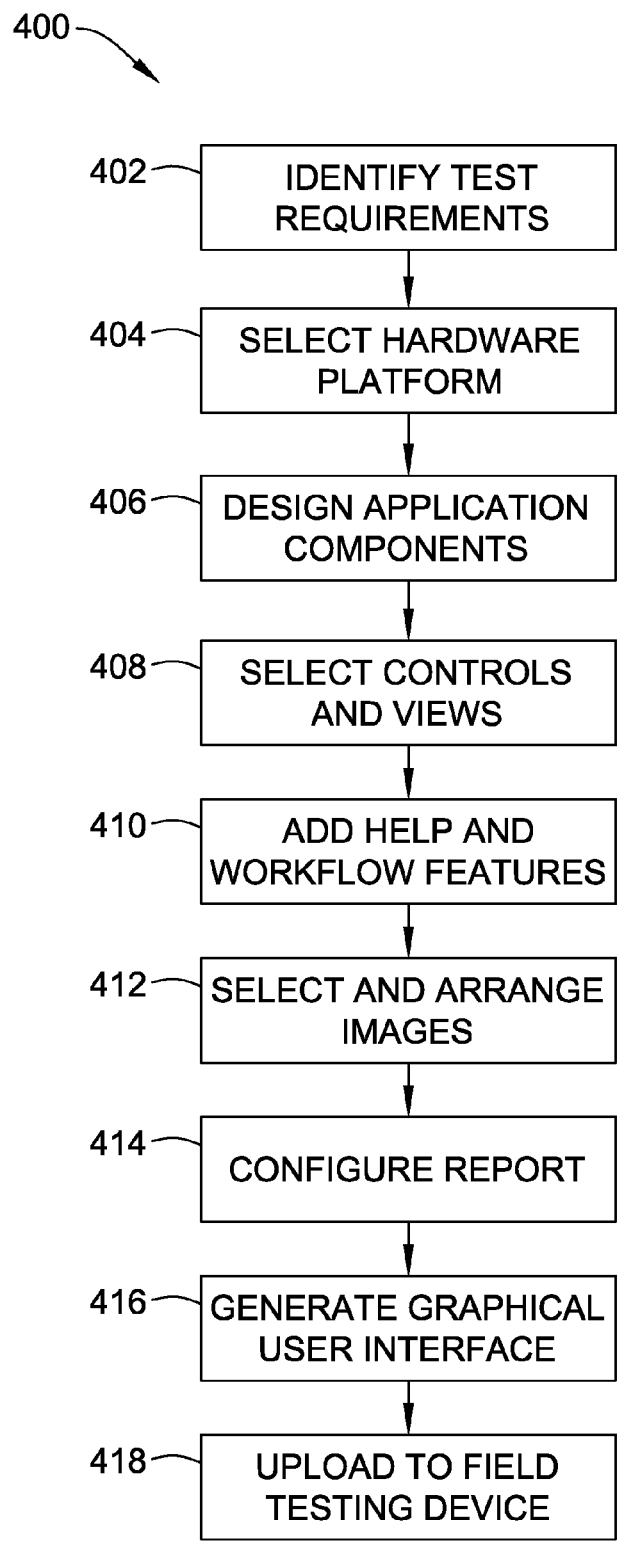
FIG. 5 is a flow diagram of an exemplary method for configuring a testing system.

FIG. 5 is a flowchart illustrating an exemplary method 400 for configuring field testing device 305. Base computing device 302 is coupled to network 332. In the exemplary embodiment, network 332 is an Internet network, an intranet network, a Wi-Fi network, a Bluetooth®-type network, an Ethernet connection, or any other suitable connection that enables method 400 to function as described herein. Field testing device 305 is also coupled to network 332 during at least portions of method 400, as described herein.

In the exemplary embodiment, using base computing device 302, an application designer 308 (shown in FIG. 3)

builds a test application, having the functions previously described, using known programming techniques, the details of which are known to those skilled in the art. Application designer 308 accesses, through a user interface on base computing device 302, application ("app") building software. In the exemplary embodiment, the app building software may be resident within base computing device 302. Alternatively, the app building software may be downloaded by application designer 308 from a network location. In another alternative embodiment, the app building software may be resident in a server (not shown) located remotely from base computing device 302, and accessed remotely via an Internet or other network connection. In alternative embodiments, application designer 308 may build a test application directly on field testing device 305 using application building software installed on field testing device 305.

Specifically, application designer 308 identifies 402 elements that the test application must address, including the device or structure to be tested, requirements imposed by applicable inspection codes or regulations, applicable service bulletins and the like. Next, application designer 308 selects 404 a type of field testing device 305 to serve as the test platform for hosting the test application and performing one or more predefined tests. After the test platform is selected 404, components that will make up the test application are selected 406. Application designer 308 then selects 408 controls (both physical and virtual) built (or programmed) into field testing device 305 that user 325 will use during the test application, and visual images that will be presented to user 325 while the test application is running. Application designer 308 may add 410 "HELP" screens and workflow screens (such as actual procedural steps for performing a test). Application designer 308 selects 412 ordering and arrangement of screens to be presented to user 325 during the test application. To complete the test application, Application designer 308 configures 414 report layout and features, and generates 416 a graphical user interface (GUI) for presenting the test application to user 325. In alternative embodiments, the GUI is automatically generated by the app building software. Following completion of the test application, the test application is uploaded 418 into a field testing device 305.

In the exemplary embodiment, the test application may be uploaded from base computing device 302 through network 332 to field testing device 305, or through a direct connection (not shown) between base computing device 302 and field testing device 305. As described herein, the test application is composed of configuration and data files. The configuration and data files are integrated with what testing functions (for example, electromagnetic, ultrasonic, etc.) that field testing device 305 is already equipped. Several different but related test applications, each involving, for example, the use of an electromagnetic sensor 306 may be uploaded into a field testing device 305, and may be selectable by user 325, by touching corresponding thumbnail icons (not shown) caused by the test application to be displayed on touch screen 350 (shown in FIGS. 4A and 4B). The test application may also include features enabling the test application to be customized to specific users, such as pre-fill or auto-fill capabilities when preparing reports (to automatically fill in the name of user 325, or other information), and the like.

In contrast to known testing systems for use in testing of structures, the testing systems and methods described herein provide user-accessible instructions and demonstration materials embodied in testing devices, enabling inexperienced users to perform tests without the need for reference to external resources, such as separate instruction or operations manuals or advice from more experienced testing personnel. The testing systems and methods described herein preclude the need for more experienced users to accompany inexperienced users into the field for tests, thus reducing manpower requirements. The testing systems and methods described herein also preclude the need for a user to carry additional note-taking or recordkeeping materials, in addition to the field testing device.

It will be appreciated that the above embodiments that have been described in particular detail are merely exemplary or possible embodiments, and that there are many other combinations, additions, or alternatives that may be included. For example, while the exemplary embodiments described herein refer to nondestructive testing of structures, the methods and systems described herein are likewise applicable to other types of testing devices and procedures. Further, while the exemplary embodiments described herein refer or suggest portable field testing devices, the methods and systems described herein are likewise applicable to other types of testing devices such as large or fixed-in-place testing devices and associated procedures.

The logic flows depicted in the figures can be implemented in any order, or may be updated sequentially, to enable the desirable results to be achieved. In addition, other steps may be provided, or steps may be eliminated, from the described logic flows, and/or other components may be added to, or removed from, the described systems. Accordingly, other embodiments are within the scope of the following claims.

The particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component.

Some portions of above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments of the invention may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture, according to the discussed embodiments of the invention. The computer readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

This written description uses examples to disclose the invention, including the best mode, and also to enable any person skilled in the art to practice the invention, including making and using any devices or systems and performing any incorporated methods. The patentable scope of the invention is formed by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A testing system for use in conducting testing of a structure, comprising:
   a testing device configured to perform electromagnetic testing, wherein the testing device comprises:
      a presentation interface comprising an electronic display device;
      a user input interface;
      a memory device;
      at least one sensor configured to acquire a plurality of field voltage and current measurement associated with the structure; and
      a processor coupled in communication with the presentation interface, the user input interface, and the memory device, the processor programmed to cause the testing device to:
         retrieve at least one demonstrative instruction for conducting a test session for preforming the electromagnetic testing using the testing device from a base computing device via a network upon receiving an input via the user input interface;
         present to a user, via the presentation interface, data comprising the at least one demonstrative instruction;
         present, via the presentation interface, at least one test instruction for use of the testing device, wherein the at least one test instruction comprises text regarding conducting the test session using the testing device; and
         simultaneously present, via the presentation interface, exemplary simulated data associated with the test session and live data associated with the test session, wherein the exemplary simulated data and the live data comprise the plurality of field voltage and current measurements associated with the structure and wherein the simulated data and the live data are depicted side-by-side.

2. The testing system in accordance with claim 1, wherein the testing device is configured to receive at least one data file containing data representing the at least one test instruction from the base computing device.

3. The testing system in accordance with claim 1, wherein the processor is programmed to cause the testing device to present to the user at least one calibration instruction for use in calibrating the testing device.

4. The testing system in accordance with claim 1, wherein the processor is programmed to cause the testing device to present to the user at least one report preparation instruction for use in preparing a report of results obtained during a test session.

5. The testing system in accordance with claim 1, wherein the at least one sensor is an electromagnetic sensor, an ultrasonic sensor, a visible light imaging device, an infrared imaging device, or an X-ray imaging device.

6. The testing system in accordance with claim 1, wherein the at least one demonstrative instruction includes an audible presentation.

7. The testing system in accordance with claim 1, wherein the presentation interface and the user input interface are coupled together as a touchscreen.

8. A testing device for conducting testing of a structure, wherein the testing device comprises:
   a sensor configured to receive sensory emanations regarding the structure, wherein the sensory emanations comprise data associated with electromagnetic testing of the structure;
   a presentation interface comprising an electronic display;
   a user input interface;
   a memory device; and
   a processor coupled in communication with the sensor, the presentation interface, the user input interface, and the memory device, the processor programmed to cause the testing device to:
      present, via the presentation interface, at least one demonstrative instruction for conducting a test session on the structure using the testing device;
      present, via the presentation interface, at least one test instruction for use of the testing device, wherein the at least one test instruction comprises text regarding conducting the test session using the testing device and audio commentary regarding conducting the test session using the testing device;
      simultaneously present, via the presentation interface, exemplary simulated data associated with the test session and live data associated with the test session, wherein the exemplary simulated data and the live data are depicted side-by-side;
      receive an indication of the completion of the test session; and
      present, via the presentation interface, at least one instruction for further courses of action after receiving the indication of the completion of the testing session, wherein the at least one instruction comprises uploading data to another device, preparing a report, or performing maintenance or shutdown procedures on the testing device.

9. The testing device in accordance with claim 8, wherein the processor is programmed to cause the testing device to present, via the presentation interface, at least one calibration instruction for use in calibrating the testing device.

10. The testing device in accordance with claim 8, wherein the processor is programmed to cause the testing device to present, via the presentation interface, at least one report preparation instruction for use in preparing a report of results obtained during the test session.

11. The testing device in accordance with claim 8, wherein the sensor is an electromagnetic sensor.

* * * * *